United States Patent [19]
Blanco et al.

[11] Patent Number: 5,348,259
[45] Date of Patent: Sep. 20, 1994

[54] FLEXIBLE, ARTICULABLE COLUMN

[75] Inventors: Ernesto E. Blanco, Belmont, Mass.; William Schnorr, Houston, Tex.

[73] Assignee: Massachusetts Institute of Technology, Cambridge, Mass.

[21] Appl. No.: 833,237

[22] Filed: Feb. 10, 1992

[51] Int. Cl.5 ............................................. E04G 3/00
[52] U.S. Cl. ................................. 248/276; 248/288.5; 248/160; 403/55; 403/56; 227/19
[58] Field of Search ............... 248/276, 288.3, 288.5, 248/160; 403/55, 56; 227/19, DIG. 1; 128/334 R, 334 C, 305, 772, 4, 5

[56] References Cited

U.S. PATENT DOCUMENTS

| | | | |
|---|---|---|---|
| 319,569 | 6/1885 | Ellis et al. | 248/288.5 |
| 2,510,198 | 6/1950 | Tesmer. | |
| 2,533,494 | 12/1950 | Mitchell. | |
| 2,776,152 | 1/1957 | Lanuzzi. | |
| 2,908,519 | 10/1959 | Holden | 248/276 |
| 3,096,962 | 7/1963 | Meijs. | |
| 3,168,274 | 2/1965 | Street | 248/276 |
| 3,584,822 | 6/1971 | Oram. | |
| 4,473,077 | 9/1984 | Noiles et al. | |
| 4,485,817 | 12/1984 | Swiggett. | |
| 4,488,523 | 12/1984 | Schichman. | |
| 4,620,813 | 11/1986 | Lacher. | |
| 4,646,745 | 3/1987 | Noiles. | |
| 4,648,733 | 3/1987 | Merkt. | |
| 4,671,445 | 6/1987 | Barker et al. | |
| 4,754,909 | 7/1988 | Barker et al. | |
| 4,796,508 | 1/1989 | Hoshino | 248/288.5 |
| 4,800,795 | 1/1989 | Yamashita | 248/288.3 X |
| 4,949,927 | 8/1990 | Madocks et al. | |
| 5,020,933 | 6/1991 | Salvestro et al. | |

FOREIGN PATENT DOCUMENTS

| | | | |
|---|---|---|---|
| 1260837 | of 1961 | France | 248/288.3 |

Primary Examiner—Alvin C. Chin-Shue
Assistant Examiner—Korie H. Chan
Attorney, Agent, or Firm—Hamilton, Brook, Smith & Reynolds

[57] ABSTRACT

A flexible, articulable column having a central cable tensioning member with a series of ball and socket members strung on the cable forming articulable joints. Each socket member has at least one conical opening with internal teeth engagable with a ball which is made of an elastomeric polymer. When the cable is tensioned, the sockets move toward each other and the balls are indented by the teeth of the socket. The column thus becomes rigid. Releasing the tension returns the column to the flexible state.

16 Claims, 4 Drawing Sheets

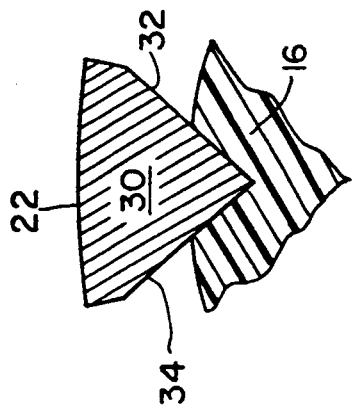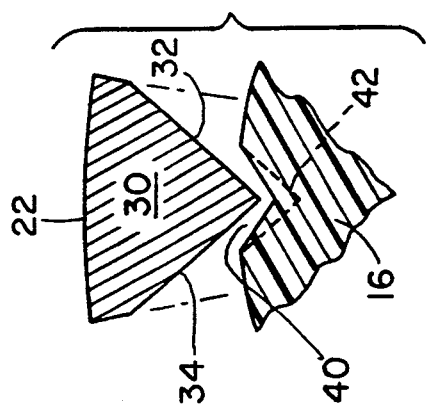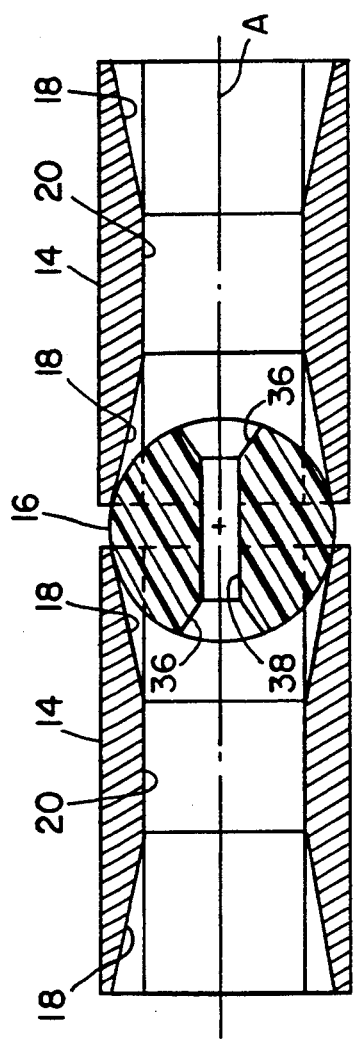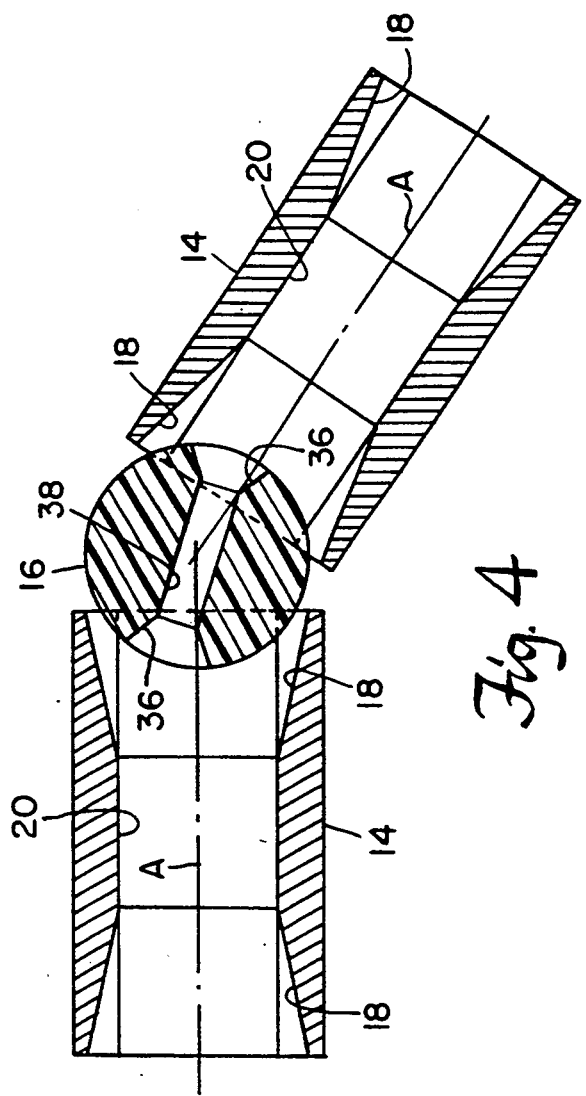

FLEXIBLE, ARTICULABLE COLUMN

FIELD OF THE INVENTION

This invention relates generally to flexible rods or columns and, more particularly, to a column which, in its natural state, is flexible and articulable, and which, by applying internal tension, such as by a cable, can be made rigid.

BACKGROUND OF THE INVENTION

Flexible columns or, as they are often called, articulable columns, have many uses. For example, they may be employed for positioning tools, as disclosed in U.S. Pat. No. 2,510,198; as article supports as, for example, for a telephone to make it is adjustable into numerous positions as taught in U.S. Pat. No. 2,533,494; as supports for electric lamps, as taught in U.S. Pat. No. 3,584,822. They may also be employed for locking measuring apparatus in position as taught in U.S. Pat. No. 3,096,962. There are many more such uses.

U.S. Pat. No. 4,949,927 discloses an articulable column and, more particularly, describes prior art columns of the ball and socket type which are flexible in their normal state and which, by application of tension from a central cable, become rigid.

Other applications of articulable, flexible columns are found in surgical staplers and particularly intraluminal staplers. Examples of intraluminal staplers with flexible shafts or columns will be found in the following U.S. Pat. Nos. 4,473,077, 4,485,817, 4,488,523, 4,671,445 and 4,754,909.

It is an object of this invention to produce an articulable, flexible column which has utility in many fields as, for example, those numerous devices as described above as well as in intraluminal staplers.

Another object of the invention is to produce an articulable, flexible column which has a relatively smooth exterior and which can produced upon being actuated, a rigid column having a greater weight to strength and weight to size than heretofore developed.

SUMMARY OF THE INVENTION

The invention is embodied in an articulable, flexible column having a central axis defined by a cable tensioning member. There are a series of ball and socket members strung along the cable to form a series of articulable joints. Each socket member has at least one generally conical opening with internal "V" shaped splines engagable with a ball. The ball is softer than the socket such that when the cable applies tension to the ball and socket members, the splines indent the balls and the column becomes rigid.

The balls are made of elastomeric polymer material such as Nylon TM, Teflon TM or Delrin TM.

The internal splines in the sockets are substantially "V" shaped in configuration and being tapered, not only indent the balls on tension being applied, but readily slide out of engagement with the balls when tension is released.

The articulable, flexible column has utility in many areas such as positioning devices control arms, locking devices, but is herein embodied in a surgical stapler of the type having staple inserting means at one end of the column and control means at the opposite end.

Functionally, when the cable control means is actuated, its tension causes a compression between the ball and socket members and the splines indent the balls to make the column rigid. At this time, staples are then fired and, when the cable tension is released, the ball and socket members slide apart and the column returns to it original or limp condition.

The internally splined socket members are harder than the balls, or, conversely, the balls are softer than the socket members such that the splines indent the balls and, being tapered, upon release of the tension, the balls and sockets slide apart.

The above and other features of the invention including various and novel details of construction in combinations of parts will now be more particularly described with reference to the accompanying drawings and pointed out in the claims. It will be understood that the particular flexible, articulable column embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 3 is a sectional view on enlarged scale of a portion of the flexible, articulable column showing two socket members and one ball in aligned relationship.

FIG. 4 is a view similar to FIG. 3 with the ball and socket members in articulated relationship.

FIG. 5 is a detail view of a spline indenting a ball when the ball and socket members are under tension.

FIG. 6 is a view similar to FIG. 5 with the spline out of the ball upon relaxation of the tension.

DETAILED DESCRIPTION

Figure 1:
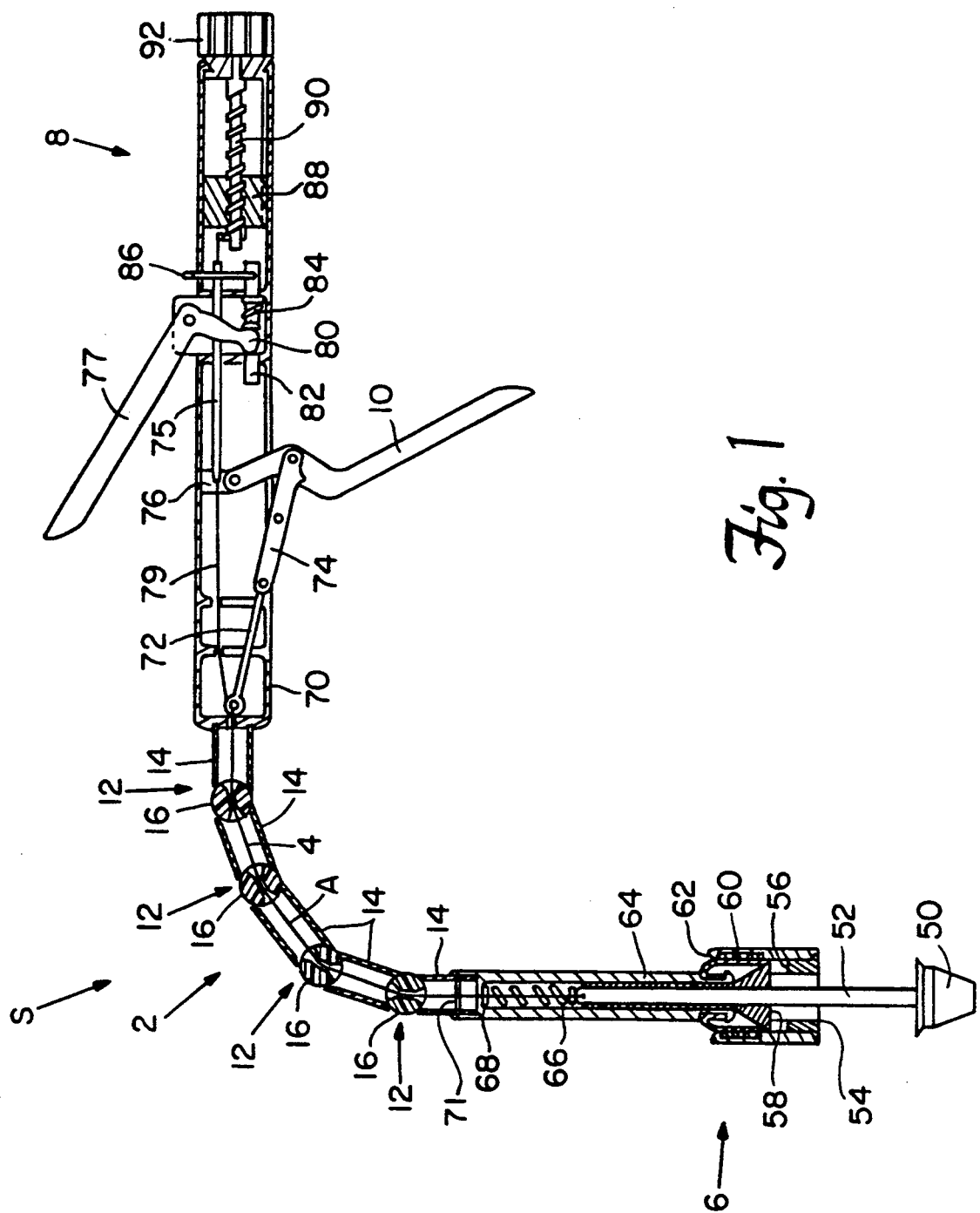
FIG. 1 is a sectional schematic view of an intraluminal surgical stapler in its flexible state embodying the invention.
Figure 2:
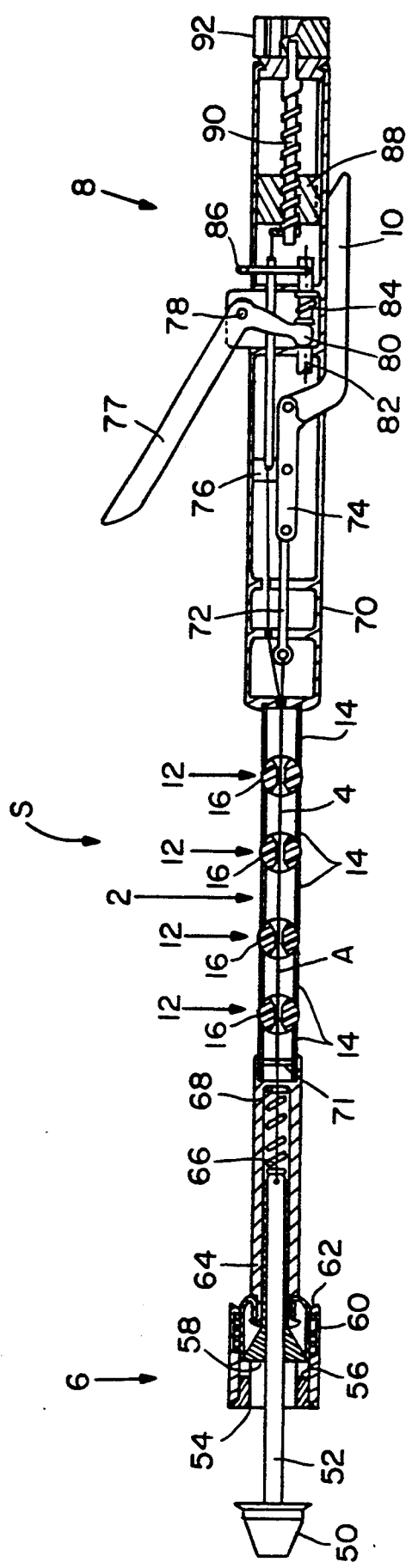
FIG. 2 is a view similar to FIG. 1 showing he stapler in its rigid condition.

FIGS. 1 and 2 show an intraluminal stapler S embodying the invention. FIG. 1 shows the stapler in relaxed or flexible condition. FIG. 2 shows the stapler in rigid condition.

It includes an articulable, flexible column generally designated 2 having an axis A defined by a cable tensioning member 4. Staple inserting means 6 are located at one end of the column 2 with cable control means 8 located at the opposite end. The stapler is normally in the flexible position of FIG. 1, but is made rigid as shown in FIG. 2 by pivoting a handle 10 from the FIG. 1 to the FIG. 2 position as will be described in more detail hereinafter. FIG. 2 shows the stapler rigid and straight, but it can be made rigid and curved as well. The flexible column 2 is made up of a series of ball and socket members generally designated 12. As herein illustrated in the stapler, the column includes five sockets 14 and four balls 16. The ball and socket members 12 are slidably strung on the cable 4. The number of ball and socket members may be increased or decreased, depending upon the use of the articulable column. The size of each element may also be varied. The manner in which the stapler is operated will be described in greater detail hereinafter.

Figure 9:
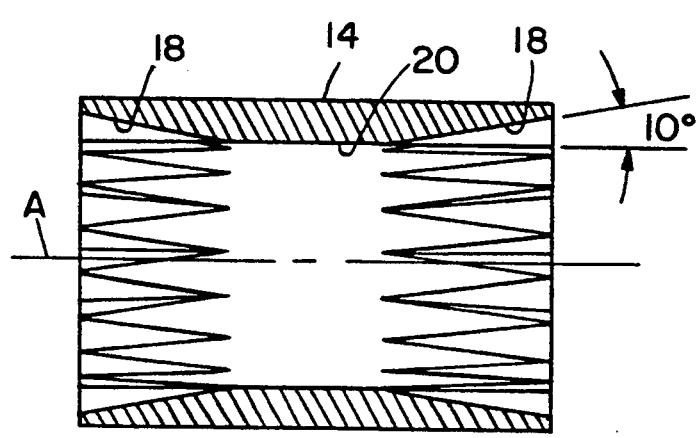
FIG. 9 is an sectional view of the socket member of FIG. 8 taken along the lines IX—IX.

Referring next to FIGS. 3 through 6, each socket member 14 has at least one generally conical opening 18 in a cylindrical body. In the illustrative example, the conical opening is formed at around a 10° angle with a cylindrical opening 20 running through the socket 14 and is best illustrated in FIG. 9. However, the angle or taper of the opening is not limited to 10°. The angle or taper of the opening 18 may also be measured from the axis A which is the geometric center of the socket 14 and along which the cable 4 extends when the device is under tension in the FIG. 2 position.

Figure 8:
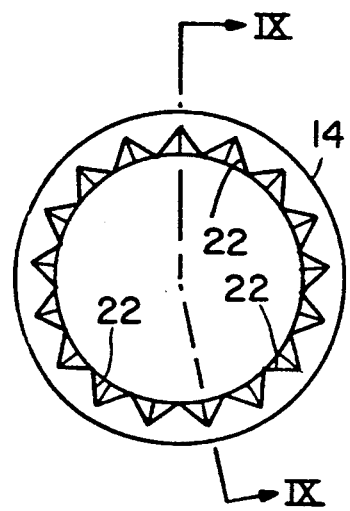
FIG. 8 is an end view of the socket member of FIG. 7.
Figure 7:
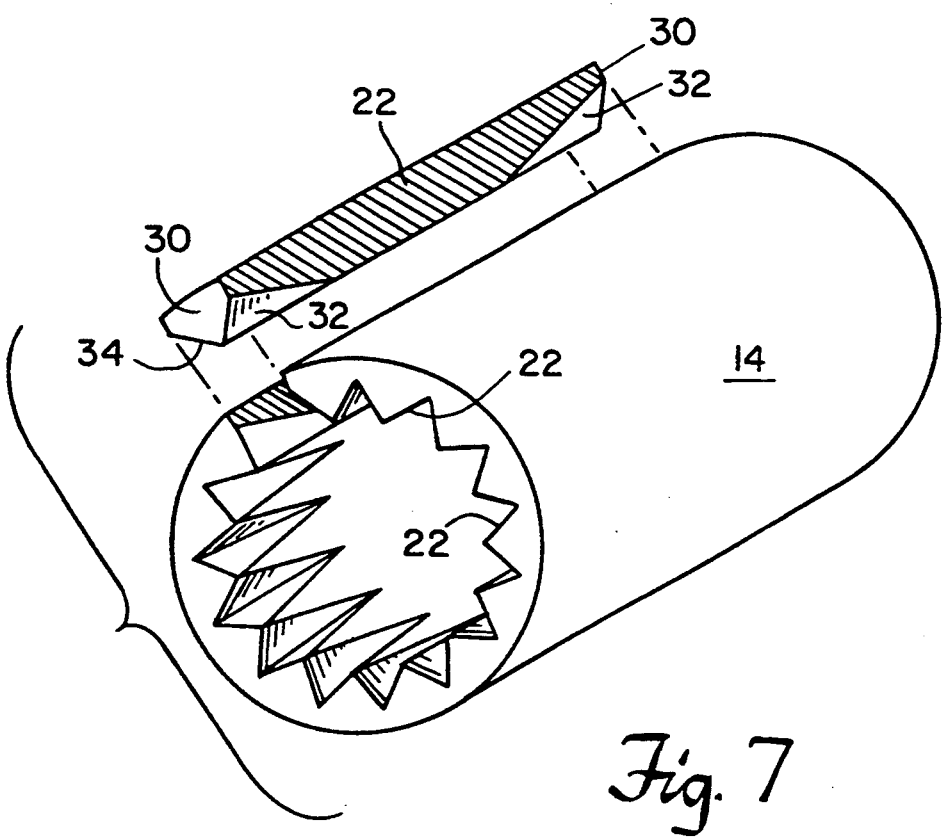
FIG. 7 is a perspective view of a socket member with one spline exploded for clarity.

As seen in FIGS. 7 to 9, inwardly extending "V" shaped splines or teeth 22 are formed in the conical opening 18. A tooth segment or spline is shown removed from the socket member 14 in FIG. 7. Each tooth has a frontal or planar surface 30 and intersecting sides 32 and 34 which are formed on the above described 10° angle. The planar surface 30 may also be called the penetrating surface and the intersecting surfaces 32 and 34 may be referred to as the exiting surfaces. As seen in FIGS. 1 and 2, when the sockets 14 engage two balls 16, there are two sets of teeth in opposite ends of the socket members 14, which is then symmetrical. When the sockets 14 engage one ball 16 or where the sockets are the end sockets of the column 2, there is only one set of teeth needed.

The sockets may be made of aluminum or any other equivalent material with sufficient hardness and strength to cause indentation in the plastic balls by the socket teeth. Aluminum was chosen because of its light weight.

The balls 16, seen in sections in FIGS. 3 and 4, comprise spheres having a conical opening 36 at each end that are joined by a cylindrical bore 38 to accommodate the cable 4 which is shown only in FIGS. 1 and 2.

The balls 16 are constructed to fit within the conical opening 18 of the socket members, but are of larger diameter than the central connecting bore 20 such that when the socket members 14 are tensioned, each ball becomes wedged in a conical portion 18 and will not pass into the conical interior 20 of the socket members. The balls are made of an elastomeric polymer having properties akin to those of Nylon TM, Teflon TM or Delrin TM and consequently are softer than the sockets.

FIGS. 5 and 6 show that upon tension being applied to the sockets, the "V" shaped teeth or splines 22 penetrate the elastometic polymer ball with the planar surface 30 indenting the ball as shown in FIG. 5. The inclined surfaces 32 and 34 are thus pressed into the ball 16. Upon the balls 16 being penetrated by the teeth 22, the system becomes rigid and is so maintained by the resistance of the balls to the shear and deformation caused by pressing the penetrating surface 30 into the elastomeric ball. The systems can become rigid, in either straight or curved form. The greater the tension applied to the socket members, the greater the force pressing the teeth into the ball and therefore the greater the amount of the penetrating surface pressed into the plastic and hence the greater the resistance to further indentation.

Upon tension being released, the teeth and balls come apart and assume the position shown in FIG. 6. A depression 40 will remain in the ball 16 with the maximum penetration being shown by the dotted "V" 42. When a plastic material such as Nylon TM, Teflon TM or Delrin TM is put under stress, it will deform; first elastically, then plastically. When the stress is released, the plastic "springs back" due to its elasticity and the balls slide outwardly of the sockets 14 along the inclined exiting surfaces 32 and 34 of the teeth. The fact that the balls have low coefficients of friction combined with elastic "spring back" or recovery, assures that the balls will slide out of the sockets upon release of tension in the cable, resulting in the column regaining its articulated flexible condition.

Referring again to FIGS. 1 and 2, the flexible, articulable column 2 will be described as part of the intraluminal stapler S.

The staple inserting means 6 includes an anvil cap 50, a staple shaft 52 to which the cap is secured, a circular cutter 54, a staple cartridge 56, an anvil/shaft guide 58, a spring 60, a staple cartridge housing 62 and an anvil and shaft housing 64. A spring 66 in the shaft housing bears on the rear end of the staple shaft 52 and against a inwardly turned portion 68 of the anvil and shaft housing 64.

A pin 71 secures the first socket 14 of the flexible column 2 to the end of the anvil and shaft housing 64. The toggle wire 4 is attached to the pin 71. The sockets 14 and the balls 16 are strung along the cable 4 from the pin 71 to the right as viewed in the FIGS. 1 and 2 to the cable control means 8 at the opposite ends of the column 2.

The cable control means 8 includes a handle housing 70 which receives a toggle shaft 72 which is pivotally attached to a bifurcated toggle joint 74 suspended by a pivot 76. The opposite end of the joint 74 is pivotably secured to the handle 10.

A staple firing arm 77 is pivotally mounted by a pin 78 and has a bifurcated end 80 received in a staple firing shaft 82. The staple firing arm 77 is urged into its open position as shown in FIGS. 1 and 2 by a spring 84 which bears against the arm 80. A jamming latch 86 is secured to the end of the staple firing shaft.

A sliding anvil cap adjustment block 88 slides in the hollow portion at the rear end of the handle housing 70. A rotatable screw 90 is threaded into the block 88 and at its right hand end is keyed to an adjustment knob 92.

The mechanism operates as follows. The stapler is inserted, in its flexible condition, into the lumen which may, for example, be an intestine. To make the flexible column 2 rigid, the toggle arm 10 is pressed toward the handle housing 70, that is, the handle 10 moves from the FIG. 1 to the FIG. 2 position. This tensions the toggle shaft 74 which, in turn, tensions the cable 4, which is attached to the pin 71 passing through the first socket 14 adjacent the housing 64 of the inserting means 6. This causes the aluminum sockets 14 to be drawn together with their teeth indenting the elastomeric balls 16 making the column 2 rigid when the stapler is in said rigid position, the adjustment knob 92 on the control end 8 of the stapler is rotated until the anvil cap 50 and the staple shaft 52 on the stapling end 6 of the stapler S have moved the desired amount. The adjustment knob 92 turns the screw 90 that is attached to the sliding adjustment block 88, thus pulling the staple adjustment shaft 75 and tensioning the staple wire 79. The wire, in turn, is attached to the staple shaft 52 which is biased by the spring 66 into extended position until the adjustment knob 92 is turned.

When the anvil cap 50 has been adjusted to the correct distance from the staple cartridge 54, the staple firing arm 77 is squeezed toward the housing 70. This, in turn, moves the staple firing shaft 82 a proscribed amount against the force of the spring 84, causing the staple firing shaft to push on a pin at the bottom of the jamming latch 86, causing the latch to tilt and engage the staple adjustment shaft 75 and move it a predetermined amount. This movement pulls the staple shaft 52 against the spring 66, and pulls the anvil cap 50 down onto the staple cartridge 54, depressing the cartridge against the spring 60. The spring 60 prevents the staple cartridge housing 62 from sliding until the anvil cap 50 is pressed onto it.

The staples, not shown, are fired by being pressed out of the staple cartridge 56 by the anvil/shaft guide 58 and then being compressed between the anvil cap 50 and the anvil shaft guide 58. Simultaneously, a new lumen is cut by the cutter 54 moving against the anvil cap 50 through the interned portions of the intestinal wall which had previously been inserted between the elements 50 and 56. Once the staples have been fired, the adjustment knob 92 may be turned in the opposite direction lessening the tension in the staple wire 79, and allowing the spin 80 to back the anvil cap off the tissue. The entire assembly may then be removed either in the rigid form or, if desired, the lever 10 may be released causing the column to again be returned to its flexible position.

We claim:

1. A flexible, articulable column having an axis defined by a cable tensioning member comprising:
    a series of balls and socket members slidably strung along the cable tensioning member to form articulable joints;
    each socket member having at least one generally conical opening with internal "V" shaped teeth engagable with one of said balls;
    the ball being softer than the socket such that when the cable applies tension, pulling the balls and sockets together, the teeth indent the balls and the column becomes rigid.

2. A flexible, articulable column having an axis defined by a cable tensioning member comprising:
    a series of elastomeric polymer balls and socket members slidably strung along the cable tensioning member to form articulable joints;
    each socket member having at least one generally conical opening with internal "V" shaped teeth engagable with one of said elastomeric polymer balls;
    the ball being softer than the socket such that when the cable applies tension, pulling the balls and sockets together, the teeth indent the balls and the column becomes rigid.

3. An articulable column according to claim 2 wherein the balls are Nylon.

4. An articulable column according to claim 2 wherein the balls are Teflon.

5. An articulable column according to claim 2 wherein the balls are Delrin.

6. A flexible, articulable column having an axis defined by a cable tensioning member comprising:
    a series of elastomeric polymer balls and socket members slidably strung along the cable tensioning member to form articulable joints;
    each socket member having at least one, generally conical, opening with substantially "V" shaped tapered internal teeth engagable with one of said elastomeric polymer balls;
    the ball being softer than the socket such that when the cable applies tension, pulling the balls and sockets together, the teeth indent the balls and the column becomes rigid.

7. An articulable column according to claim 6 wherein the balls are Nylon.

8. An articulable column according to claim 6 wherein the balls are Teflon.

9. An articulable column according to claim 6 wheien the balls are Delrin.

10. A surgical stapler comprising:
    a flexible, articulable column having an axis defined by a cable tensioning member;
    staple inserting means at one end of the column and cable control means at the opposite end;
    a series of plastic balls and socket members slidably strung along the cable to form articulable joints;
    each socket member having at least one generally conical opening with internal teeth engagable with one of said plastic balls;
    the ball being softer than the socket such that, upon the cable control means being actuated, the cable applies tension, pulling the balls and sockets together, the teeth indenting the balls to make the column rigid whereupon staples are fired, and when the cable tension is released, the column returns to flexible condition.

11. A surgical stapler according to claim 10 wherein the balls are Nylon.

12. A surgical stapler according to claim 10 wherein the balls are Teflon.

13. A surgical stapler according to claim 10 wherein the balls are Delrin.

14. An articulable column according to claim 1 wherein balls are Nylon.

15. An articulable column according to claim 1 wherein balls are Teflon.

16. An articulable column according to claim 1 whetrein the balls are Delrin.

* * * * *